(12) United States Patent
Compton et al.

(10) Patent No.: US 7,919,649 B2
(45) Date of Patent: *Apr. 5, 2011

(54) PLASTICISER ESTERS

(75) Inventors: Brady Compton, Baton Rouge, LA (US); John Lyford, IV, Baton Rouge, LA (US); Nicolaas A. De Munck, Barendrecht (NL); Aad Gerrit Oskam, Rozenburg (NL); Allen D. Godwin, Seabrook, TX (US); Leendert Johannes Van Dop, Rozenburg (NL)

(73) Assignee: ExxonMobile Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/398,235

(22) Filed: Apr. 5, 2006

(65) Prior Publication Data

US 2006/0270868 A1 Nov. 30, 2006

Related U.S. Application Data

(60) Provisional application No. 60/685,616, filed on May 27, 2005.

(51) Int. Cl.
*C07C 67/08* (2006.01)

(52) U.S. Cl. .......................................................... 560/78

(58) Field of Classification Search ...................... 560/78
See application file for complete search history.

(56) References Cited

U.S. PATENT DOCUMENTS

| 5,324,853 | A | | 6/1994 | Jones et al. ...................... 560/98 |
| 5,460,885 | A | * | 10/1995 | Chu-Ba ........................ 428/383 |
| 5,880,310 | A | | 3/1999 | Ageishi et al. ................. 560/99 |
| 6,150,552 | A | | 11/2000 | Schreier et al. ................ 560/78 |
| 2004/0254393 | A1 | * | 12/2004 | Godwin et al. ................. 560/98 |

FOREIGN PATENT DOCUMENTS

WO  WO 2005/021482  10/2005

* cited by examiner

*Primary Examiner* — Shawquia Young
(74) *Attorney, Agent, or Firm* — Leandro Arechederra, III; Andrew B. Griffis

(57) ABSTRACT

Esters produced by the catalyzed reaction of alcohols and acids or anhydrides are neutralized by treatment with an aqueous alkaline alkali metal salt solution in an amount that provides less than a stoichiometric amount of alkali metal salt in relation to the acidity of the crude ester and the amount of water present during the treatment is from 0.7 to 1.4 wt % of water based on the weight of crude ester. When using titanium as the esterification catalyst, the ester resulting from this process contains less than 0.01 ppm by weight of titanium residue, so that it is storage stable when stored in the presence of an antioxidant.

6 Claims, No Drawings ial Applica-

PLASTICISER ESTERS

CROSS REFERENCE TO RELATED APPLICATIONS

This application claims the benefit of Provisional Application No. 60/685,616 filed May 27, 2005, the disclosure of which is incorporated by reference.

BACKGROUND

The present invention relates to the production of esters such as plasticisers and lubricants, particularly but not exclusively to the production of phthalate ester and benzoate ester plasticisers (which are useful in polyvinyl chloride, PVC) and polyisocyanate compositions (which are useful in the production of polyurethanes).

Plasticiser esters are produced by reaction of the appropriate alcohol, typically a $C_4$ to $C_{13}$ alcohol, with an acid anhydride, frequently phthalic anhydride, cyclohexane dicarboxylic acid anhydride, trimellitic anhydride, maleic anhydride, or with an acid. Acids frequently used are adipic acid, trimellitic acid, cyclohexanoic mono- and dibasic acids, benzoic acid, citric acid and the like. The esterification is typically performed using an organo-metallic catalyst particularly a titanium or tin based catalyst, but many other esterification catalysts like sulfuric acid and para-toluene sulfonic acid are also known. The term crude ester as used herein, means the product of esterification, which will contain contaminants and requires purification. These contaminants can belong to the family of acidic residues, unreacted alcohol or unreacted acid, catalyst residues, water and the contaminants that were already present in the alcohol feed, most of these being so-called monomeric components and showing up in the so-called "light ends" region of the Gas Chromatogram or GC-spectrum of the ester. The esters can also contain byproducts, such as alcohol (di-alkyl) ethers, mono-esters from dibasic acids, alcohol oxo acid esters, hemiacetals and vinyl ethers. These are so-called dimeric components and are often collectively called "ethers" or "intermediates" due to their elution in the Gas Chromatogram or GC-spectrum of the ester between the monomeric light ends and the "trimeric" diesters.

It is known from U.S. Pat. No. 5,324,853 to purify esters of dicarboxylic acids or anhydrides by contacting the crude ester with aqueous alkali such as sodium hydroxide or sodium carbonate. The addition of the water and the alkali hydrolyses and/or neutralises catalyst residues and neutralises any undesirable mono-ester that may be present. The neutralized ester is then typically filtered for the removal of salts such as the alkali salts of the mono-esters, the hydroxide of the organo-metal catalyst such as titanium hydroxide, the oxide of the organo-metal catalyst such as titanium dioxide or tin oxide, and sodium (bi-)carbonate. The alkali used for the neutralization is preferably sodium carbonate or in some instances it may be sodium hydroxide, preferably in an aqueous form. The hydrolysis and/or neutralisation may be followed by injection of carbon dioxide to convert any remaining sodium hydroxide into water and sodium (bi) carbonate. Finally any excess alcohol and water may be removed by flashing or stripping with a vapor, e.g. with steam or nitrogen, or by a combination thereof.

Example 5 of U.S. Pat. No. 5,324,853 describes the neutralization of an ester obtained from phthalic anhydride and isodecyl alcohol using tetra-isopropyl titanate as an esterification catalyst. The neutralization is effected with a dilute solution of soda ash containing enough soda ash to provide 1.5 to 2 stoichiometric equivalents of sodium carbonate and enough water to provide from 1 to 6 wt % water based on the batch. The temperature for the treatment can be from 70° C. to 120° C. although the acceptable temperature range is said to be from 90° C. to 140° C. U.S. Pat. No. 5,324,583 suggests that carbon may be added before the start of hydrolysis so that decolouring can occur at the same time as the neutralization and hydrolysis. It also describes the addition of clay or filter aid after hydrolysis and before filtration. However, this does not address the problem that there is a tendency for the titanium hydroxide and the salts formed in the neutralization reaction to agglomerate or gel together, rendering it difficult to remove by filtration.

We have found that the purification process described in Example 5 of U.S. Pat. No. 5,324,853 suffers from two disadvantages. Firstly, the levels of excess soda ash used are such that they can lead to undesirably high levels of sodium in the final plasticiser ester. This in turn can cause the plasticiser to initiate undesirable pre-polymerization of isocyanates when it is used as a solvent for the isocyanate in the production of polyurethanes, and may impair the electrical properties when used, for example, in wire and cable insulation. Secondly, on an industrial scale where several hundred tonnes of material are to be filtered, the levels of water used in U.S. Pat. No. 5,324,853 can cause a rapid increase in the pressure drop across a filter leading to a reduction in filtration efficiency and also a reduction in the life of the filter.

The pressure drop in a filter is the difference between the inlet pressure at the filter and the outlet pressure and primarily is the pressure loss over the filter cake. If the pressure drop becomes too high, the filter cake becomes compacted, so inhibiting filtration, and furthermore the filter cake can become difficult to remove. In the process of U.S. Pat. No. 5,324,583 water is removed before filtration by flashing as rapidly as possibly. In an industrial scale process this typically involves performing the neutralization at from 100° C. to 140° C. so that the temperature is such that the water may readily be flashed off.

Plasticiser esters (also termed simply "plasticisers" herein) may be used as solvents for isocyanates in the production of polyurethanes. The plasticiser is typically used in an amount of 20 to 40 wt % of the polyurethane. The isocyanate is dissolved in the plasticiser and this solution is mixed with a polyol to produce polyurethanes. The plasticiser acts as a carrier for the isocyanate and also as a plasticiser for the polyurethane. Typical uses for such polyurethanes include mastics and sealants such as those used in the assembly of glass and in the building, aerospace and automobile industries. It is important that the plasticiser does not adversely affect the isocyanate. We have found that the levels of residual sodium or base that can be present when using the preferred ester finishing technique of U.S. Pat. No. 5,324,853 can cause pre-polymerization of the isocyanate before it reacts with the polyol, leading to undesired gel and sediment formation.

The properties and quality requirements for plasticisers depend upon the use to which the plasticiser is to be put. The requirements with isocyanates have been discussed above. Another important property of a plasticiser is its electrical resistivity, particularly when it is to be used in electrical applications such as for wire and cable insulation. More specifically, the present invention also relates to a process which can be combined with the process of our copending PCT patent application WO 2005021482 to produce a high quality plasticiser ester suitable for use with polyvinyl chloride which is to provide a composition useful for wire and cable insulation and as other electrical insulating material.

Plasticised polyvinyl chloride is widely used for insulation in the electrical and electronic industries and these uses require a high-quality plasticiser ester. For example, a plasticiser having high volume resistivity is required in the electrical field. The resistivity of a plasticised polyvinyl chloride composition may be measured as the Pad Volume Resistivity (PVR). Many people in the industry measure also the resistivity of the plasticiser itself, which is known as the liquid volume resistivity (LVR) of a plasticiser. For several electrical applications like e.g. the electrical insulation of under-the-hood or under-the-dashboard electrical wire and cables in vehicles, plasticisers are preferred to have a high LVR, and a low amount of light ends, especially those compounds that contribute to odor and automotive interior and windscreen fog problems. The electrical equipment in vehicles is becoming more and more complex and sophisticated. Modern vehicles are being increasingly equipped with extra sensors and electrically driven devices. The amount of wiring and cabling necessary for connecting these sensors and controlling and powering these devices continues to increase. Many of these connections are placed out of sight under the vehicle upholstery and relatively close to the outer body, where there is little ventilation and temperatures may be high due to engine heat or exposure of the vehicle to sunshine.

Accordingly, in addition to the low sodium levels discussed previously, plasticisers desirably should have an acceptable odor, and should not cause fogging or the creation of a light scattering film on the innerside of car windshields; they should also be resistant to ultra violet light. The plasticiser should contain only minimal amounts of volatiles or light ends in order to have a low odor level both during its processing and in its final application.

U.S. Pat. No. 5,880,310 is concerned with purifying plasticiser esters to produce materials with high liquid volume resistivity as measured by Japanese Industry Standard JIS K-6751. U.S. Pat. No. 5,880,310 obtains high volume resistivity of a plasticiser ester by blowing carbon dioxide into the crude ester that has been neutralized with sodium hydroxide to convert residual alkali into a (bi-) carbonate; recovering any excess alcohol, typically by steam stripping; and then by adding a filter aid to the neutralized and stripped ester followed by fine filtration and adsorption treatment. This process, however, uses excess sodium. Furthermore the process does not perform the neutralization in the presence of a filter aid and there remains a tendency for the products of hydrolysis of the titanium-containing catalyst to agglomerate and impair filterability.

DESCRIPTION

The present invention provides improvements in the purification of plasticiser esters, and in particular improvements that provide plasticiser esters that may be used as solvents for isocyanates in the production of polyurethanes with a reduced tendency to cause the isocyanate to pre-polymerize. The invention is also concerned with improving the filterability of the esters. The invention is also aimed at providing plasticiser esters of an improved purity that are particularly well suited for use in PVC electrical insulation for high resistivity products.

According to the present invention there is provided a process for the purification of a crude ester produced by the reaction of an acid or anhydride and an alcohol in the presence of an esterification catalyst, which process comprises treating the crude ester with an alkaline aqueous solution of an alkali metal salt wherein less than a stoichiometric amount of the alkali metal in relation to the acidity of the crude ester is employed and the amount of water present during the treatment is from 0.7 to 1.4 wt % based on the weight of crude ester.

The amount of water present during the treatment is made up of water added as part of the purification process, and water already present in the crude ester after the esterification process. In typical commercial processes this latter (already-present) water amount is in the range 30-60 ppm bij weight. Therefore the already-present amount is usually negligible compared with the water employed in the aqueous alkaline solution used according to the invention.

Preferably, sodium or potassium is used as the alkali metal for the treatment of the crude ester. Preferred salts of the alkali metals are the hydroxides or the carbonates or bicarbonates. Hydroxides may be used in combination with addition of carbon dioxide, in order to convert any remaining unreacted hydroxide to the (bi)carbonate, which is easier to remove by filtration. Most preferred alkali metal salts are sodium or potassium carbonate, in particular sodium carbonate. We have found that sodium carbonate offers a wider operating window (compared to sodium hydroxide) within which a good filter cake may be made, as explained later.

The treatment of the crude ester neutralizes any residual acidity which may result from unesterified acids or anhydrides or partially esterified polycarboxylic acids or anhydrides. In addition, the treatment can hydrolyse catalyst residues, which is particularly useful when employing titanium catalyst, where the hydrolysis converts the catalyst residues to titanium hydroxide, which can be removed by filtration.

In a preferred embodiment of the present invention the esterification catalyst is a titanium catalyst.

According to the invention, the treatment of the crude ester is preferably performed at a temperature in the range 100° C. to 140° C.

In a further preferred embodiment, the treatment is performed at elevated pressure sufficient to prevent the water vaporizing such as from 4 to 10 bar gauge (or barg), preferably from 5 to 6 barg.

In a further preferred embodiment of the present invention, following treatment the ester is subjected to a flash, preferably under vacuum, to remove water. This preferably removes free water and/or reduces the water content to 500 ppm by weight or lower.

In a further preferred embodiment of the present invention, the neutralized crude ester is subjected to filtration. The filtration preferably takes place after the flash to remove water. Removing water prior to filtration has several benefits. It promotes the conversion of titanium hydroxide into titanium dioxide, which is easier to filter. It also makes the sodium salt of any remaining mono-ester less sticky and therefore easier to filter out. Also, the sodium bicarbonate, which makes up most of the filter cake in the filtration step, forms better crystals when dehydrated, which provide for smoother filtration. In a further preferred embodiment, a filtration aid is provided to the crude ester before, during or after its treatment with the aqueous alkaline solution, for example a sodium carbonate solution. This filter aid has the important function of preventing the crystals, typically of sodium bicarbonate, from forming a dense and low porosity layer on the filter cloth, and quickly blocking up the filter. In a yet further embodiment, an adsorbent such as activated carbon is added to the crude ester before, during or after its treatment with the aqueous alkaline solution, for example a sodium carbonate solution, preferably together with a filtration aid. The adsorbent will provide product having a lower colour.

Examples of filter aids that may be used are a filter aid produced from diatomaceous earth, which is widely marketed

[for example, Radiolite (made by Showa Kagaku Kogyo K. K.) and Celite (made by Johns Manville Sales Corp.)]; a filter aid produced from perlite [for example, Topco Perlite (made by Showa Kagaku K. K.) and Dicalite Perlite (made by Dicalite Orient K. K.)] and the like are mentioned. We prefer that at least 20% of the filter aid has a particle size of 5 microns (μm) or less.

An alternative to the preferred dry filtration is to filter with the water present, so that most of the titanium is still present as titanium hydroxide and removed as such. Downstream of the filter, the free water may then be separated off by physical phase separation, and this free water may contain most of the remaining salts in solution.

Catalysts

The esters to which the present invention applies are typically plasticiser esters produced by the catalytic reaction of acids, generally polycarboxylic acids or anhydrides, and alcohols. The esterification process is conducted in the presence of a catalyst. Typical esterification catalysts of commercial importance are sulfuric acid, methane sulfonic acid (MSA), para-toluene sulfonic acid (pTSA), stannous alcoholates, alkoxides, carboxylates, chelates or oxides, and titanium alcoholates. U.S. Pat. No. 3,056,818, incorporated herein by reference, discloses titanium esterification catalysts, the more commonly used catalysts being tetra-isopropyl titanate, tetra-butyl titanate, tetra-n-butyl titanate, tetra-isobutyl titanate, and/or tetra-octyl titanate, preferably tetra-isooctyl titanate. More details on how the esterification process may be conducted, may be found in U.S. Pat. Nos. 5,324,853, 5,880,310 and 6,355,817, or in copending PCT patent application WO 2005021482, which are incorporated herein by reference.

Typical titanium alcoholates which can be used as catalysts are esters of hypothetical orthotitanic acid $Ti(OH)_4$, including tetramethyl titanates, tetraethyl titanates, tetrapropyl titanates, tetra-isopropyl titanates, tetrabutyl titanates (both normal and isobutyl), tetrapentyl titanates, tetrahexyl titanates, tetraheptyl titanates, tetra-octyl titanates, tetranonyl titanates, tetradecyl titanates, tetra-(2-propylheptyl) titanates, tetradodecyl titanates, tetrahexadecyl titanates, tetra-octadecyl titanates and tetraphenyl titanates. With many of these titanates, the iso equivalents are often preferred over or used in combination with the straight chain alternatives because they provide a lower viscosity and pour point. The choice of the titanate may depend on the alcohol being esterified. For $C_8$ to $C_{10}$ alcohols, we prefer to use also a $C_8$, $C_9$ and/or $C_{10}$ titanate. These also provide a lower viscosity than their longer chain equivalents. The alkoxy groups on the titanium atom can all be the same or they can be different; the alkyl chains of the alkoxy groups may be unbranched or branched or a mixture thereof. The zirconium counterparts of the above alcoholates can be used as a substitute in whole or in part as catalysts. Titanium carboxylates and chelates, and their zirconium counterparts, may also serve as esterification catalysts.

Acids

Carboxylic acids which undergo esterification can be aliphatic, cyclo-aliphatic or aromatic. They can be substituted or unsubstituted, saturated or unsaturated, or they can be blends of acids. Representative acids include acetic, hydroxyacetic, chloroacetic, bromoacetic, cyanoacetic, 5-phenylacetic, triphenyl acetic, propionic, halopropionic, lactic, beta-hydroxy propionic, n-butyric, isobutyric, n-valeric, 2-methyl butanoic, 3-methyl butanoic, 5-phenyl-n-valeric, n-heptanoic, caproic, pelargonic, caprylic, lauric, palmitic, lignoceric, alpha-hydroxy lignoceric, malonic, succinic, glutaric, adipic, pimelic, azelaic, sebacic, decane-1,10-dicarboxylic, pentadecane-1,15-dicarboxylic, pentacosane-1,25-dicarboxylic, 1,2,3-propane tricarboxylic, citric, acrylic, alpha-chloro acrylic, beta-chloro acrylic, beta-bromo acrylic, beta-phenyl acrylic, methacrylic, vinyl acetic, crotonic, angelic, tiglic, undecylenic, oleic, erucic, linoleic, linolenic, maleic, fumaric, mesaconic, citraconic, itaconic, mucconic, aconitic, myristic, stearic, isostearic, branched $C_5$, $C_6$, $C_7$, $C_8$, $C_9$, $C_{10}$, $C_{11}$, $C_{12}$ or $C_{13}$ oxo-acids (e.g. 3,5,5-trimethylhexanoic acid), and branched $C_{16}$, $C_{18}$, $C_{20}$, $C_{24}$, $C_{26}$, $C_{28}$, $C_{32}$, $C_{36}$, $C_{40}$, $C_{44}$ or $C_{48}$ acids, which may be derived using the Guerbet reaction and oxidation.

Among the cyclo-aliphatic acids are cyclopropane carboxylic, cyclobutane carboxylic, cyclopentane carboxylic, cycloheptane carboxylic, cyclohexane carboxylic, 2-hydroxy cyclohexane carboxylic, 1,1-cyclopropane dicarboxylic, 1,2-cyclobutane dicarboxylic, 1,3-cyclobutane dicarboxylic, 1,2- or 1,3- or 1,4-cyclohexane dicarboxylic, cyclohexane-1,2,3, 4,5,6-hexacarboxylic, cyclopentene-2-carboxylic, 1-cyclohexene-1-carboxylic, cyclohexadiene-1,2-dicarboxylic, and 1,3-cyclohexadiene-1,4-dicarboxylic.

The aromatic acids include benzoic, o-, m- and p-chloro and bromo benzoic, o-, m- and p-hydroxy benzoic, o-, m- and p-nitrobenzoic, o-, m- and p-methoxy benzoic, alpha-naphthoic, beta-naphthoic, o-, m- and p-methyl benzoic, o-, m- and p-ethyl benzoic, p-phenyl benzoic, phthalic, isophthalic, terephthalic, hydroxy phthalic, 2,3-dimethyl benzoic, benzene-1,2,4-tricarboxylic, benzene-1,3,5-tricarboxylic, benzene-1,2,4,5-tetracarboxylic, diacids of naphthalenes and trimellitic acid.

When polyols are used to form an ester treated in accordance with the invention, the following acids are preferred: isopentanoic acid, neopentanoic acid, neoheptanoic acid, neo-octanoic acid, neononanoic acid, neodecanoic acid, 2-ethyl hexanoic acid, oxo-heptanoic acid (i.e., a mix of isomers derived from oxonation/oxidation of hexenes), 2-propyl heptanoic acid, oxo-decanoic acid (i.e., a mix of isomers derived from oxonation/oxidation of mixed nonenes), oxo-octanoic acid (i.e., a mix of isomers derived from oxonation/oxidation of mixed heptenes), 3,5,5-trimethylhexanoic acid, linear C5-C18 alkanoic acids, in particular n-pentanoic, n-heptanoic and n-nonanoic acid, and blends thereof.

Anhydrides

Anhydrides of mono and dibasic acids can be used in place of the acids, especially when plasticiser esters are being formed. These include acetic anhydride, propionic anhydride, n-butyric anhydride, succinic anhydride, glutaric anhydride, adipic anhydride, pimellic anhydride, maleic anhydride, mesaconic anhydride, citraconic anhydride, glutaconic anhydride, itaconic anhydride, phthalic anhydride, benzoic anhydride, nadic anhydride, methyl nadic anhydride, hexahydrophthalic anhydride, trimellitic anhydride and mixed anhydrides of monobasic acids. Another anhydride which may be used is pyromellitic dianhydride. Also, tetrabromo phthalic anhydride may be used for ester production.

Alcohols

Among the alcohols which may be reacted with acids and anhydrides to form the crude esters treated according to the invention are, by way of example, most primary and secondary $C_1$-$C_{30}$ monohydric, substituted or unsubstituted alkanols and alkenols, such as, methanol, ethanol, chloroethanol, cyanoethanol, ethoxy-ethanol, phenylethanol, n-propanol, 2-chloropropanol-1, 3-bromopropanol-1, 2,2-dichloropropanol-1, isopropanol, 2-nitrobutanol-1, 2-nitrobutanol-4, 2-methylpentanol-1, 2-methyl pentanol-3, the primary and secondary octanols, n-dodecanol, 6-dodecanol, lauryl, myristyl stearyl and isostearyl alcohol, 2-propenol-1, 2-butenol-1, 3-pentenol-1, ethylene glycol, trimethylene glycol, tetramethylene glycol, pentamethylene glycol, tetraethylene glycol, glycerol, 1,4-butanediol, mono and technical grade (i.e., 88% mono, 10% di and 1-2% tri) pentaerythritol, decane-1,10-diol, pentadecane-1,15-diol, pentacosane-1,25-diol, 2,4-hexadiene-1,6-diol, 2,4-octadiene-1,8-diol, and aromatic alcohols such as benzyl alcohol, o-, m- and p-methoxy alcohol, o-, m- and p-nitrobenzyl alcohol, o-, m- and p-methyl benzyl alcohol, phenyl ethyl alcohol, triphenyl ethyl alcohol, o-, m- and p-benzyl benzyl alcohol, alpha-naphthyl-ethyl alcohol, beta-naphthyl ethyl alcohol, naphthylene-1,2-diethyl alcohol, phenylene-1,3,5-triethyl alcohol, and phenylene-1,4-dioctyl alcohols. This includes higher Guerbet alcohols which are beta carbon branched dimer alcohols having 10 to 48 carbon atoms. Of particular importance are oxo-alcohols with 4, 5, 6, 7, 8, 9, 10, 11, 12 or 13 carbon atoms, as single carbon numbers or as mixtures thereof, with unbranched or branched alkyl chains or mixtures thereof, including those made via aldolisation such as 2-methyl pentanol, 2-ethyl hexanol, 2,4-dimethyl heptanol, 2-propyl heptanol and the like.

Polyols (i.e., polyhydroxy compounds) are represented by the general formula:

$R(OH)_n$ wherein R is an alkyl, alkenyl or aralkyl hydrocarbyl group and n is at least 2, and can be used in place of the mono alcohols when polyol esters are the desired esters to be treated in accordance with the invention. The hydrocarbyl group may contain from about 2 to about 20 or more carbon atoms, and the hydrocarbyl group may also contain substituents such as chlorine, nitrogen and/or oxygen atoms. The polyhydroxy compounds generally will contain from about 2 to about 10 hydroxy groups and more preferably from about 2 to about 6 hydroxy groups. The polyhydroxy compound may contain one or more oxyalkylene groups and, thus, the polyhydroxy compounds include compounds such as polyetherpolyols. The number of carbon atoms and number of hydroxy groups contained in the polyhydroxy compound used to form the carboxylic esters may vary over a wide range. Also, not all of the hydroxy groups necessarily need to be esterified. Esters containing free hydroxy groups may be produced by only partially esterifying the hydroxy groups on polyhydroxy compounds used as starting materials.

The following alcohols are particularly useful as polyols: neopentyl glycol, 2,2-dimethylol butane, trimethylol ethane, trimethylol propane, trimethylol butane, mono pentaerythritol, technical grade pentaerythritol, dipentaerythritol, ethylene glycol, propylene glycol and polyalkylene glycols (e.g., polyethylene glycols, polypropylene glycols, polybutylene glycols, etc., and blends thereof such as a polymerized mixture of ethylene glycol and propylene glycol).

The present invention is also useful in purifying polyol esters, such as neopolyol esters, formed from polyols and excess fatty acids. The polyol or polyol mixture preferably comprises technical grade pentaerythritol (PE), trimethylolpropane (TMP), and neopentylglycol, each of which can be admixed with monopentaerythritol and/or trimethylolpropane or other neopolyols. The preferred acid component for use with polyols to produce a polyol ester to be treated according to the invention is typically a mixture of straight chain acids having 5 to 10 carbon atoms, and/or branched chain acids having from 5 to 18 carbon atoms, preferably 5 to 9 carbon atoms, including 2-methyl butanoic acid, 3-methyl butanoic acid, 2-methylpentanoic acid, 2-methylhexanoic acid, 2-ethylpentanoic acid, 2-ethylhexanoic acid, 2,4-dimethylheptanoic acid, 3,5,5-trimethylhexanoic acid, 2-propyl heptanoic acid or mixtures thereof. Generally, the acids are monocarboxylic acids. Suitable straight chain acids include, but are not limited to, valeric acid (C5), enanthic acid (C7), caprylic acid (C8), pelargonic acid (C9), and capric acid (C10).

The branched chain acid may be for example iso-C5, iso-C7, iso-C8 or iso-C9. Preferably, the branched chain acid used is the iso-C7 acid. Another preferred branched acid is 3,5,5-trimethylhexanoic acid derived from the oxonation/oxidation of di-isobutylene. Still another preferred branched acid is oxo-octanoic acid derived from the oxonation/oxidation of mixed heptenes.

In the reaction used to form esters, one of the reagents is typically used in excess, making the other reagent the limiting reagent. This results in the acid or anhydride or a mixture of them, or the alcohol or polyol or a mixture of them, being present in an excess, for example an excess of about 10 to 50 mole percent or more for the amount of limiting reagent used. The excess reagent is used to force the reaction to completion. The composition of the feed reagents may be adjusted so as to provide the desired composition of product ester. After the reaction is complete, the excess reagent is removed by suitable means such as stripping and additional finishing.

A preferred process for the production of the esters is described in U.S. Pat. No. 5,324,853 in which a process is disclosed for the catalytic esterification of acids or anhydrides with a mono-alcohol or a polyhydroxy compound. This process comprises the steps of adding either an acid or anhydride and a mono-alcohol or a polyhydroxy compound to a reaction vessel to form a reaction mixture, and heating the reaction mixture to a temperature in the range between about 150 to 280° C., preferably between about 180 to about 260° C. The pressure is maintained at a level sufficient to obtain boiling of the reaction mixture, thereby causing the esterification and removing water as vapor, while continuously mixing the reaction mixture in the reactor vessel such that there is a reactor turnover rate of at least about 2.5 to about 20. In the foregoing, reactor turnover rate is defined to be the volume of reaction mixture internally recirculated per minute divided by the reaction mixture volume. In this way the rate of conversion is enhanced, such that for plasticiser esters limiting reagent conversions of greater than 99% are achieved and such that for polyol esters limiting reagent conversions of greater than 98% are achieved. It is still possible to heat the reagents at higher temperatures, such as up to 350° C., so long as the reagents, including the catalyst, remain stable.

Optionally in the process of U.S. Pat. No. 5,324,853, the step of heating the reagents may use a reflux drier or non-reflux drier method for reducing the amount of water refluxed from the vapor taken overhead from the reaction vessel.

The non-reflux drier method of U.S. Pat. No. 5,324,853 includes the following steps: passing vapor from the reaction vessel through a condenser and then passing the condensate to an overhead collection drum which allows the excess reagent and the water to separate into two liquid phases; separating the excess reagent from the water; recycling the excess reagent through a heater and to a flash drum thereby producing a water-rich vapor which is taken out overhead and combined with the vapors from the reaction vessel and an excess reagent-rich liquid which is recycled to the reaction vessel; optionally recycling the water to the hydrolysis step; also optionally taking the vapors from the overhead collection drum for condensation of water contained therein; and if desired, recycling condensate from the vapors to the hydrolysis step.

The reflux drier method includes the additional steps of: passing vapor from the reaction vessel through a packed or trayed, preferably a packed, tower or column such that a portion of excess reagent contained within the vapor is condensed and recycled to the reaction vessel, and wherein the remaining vapor is taken overhead; passing the remaining vapors through a condenser to an overhead collection drum which allows the excess reagent and the water to separate into two liquid phases; separating the excess reagent from the water; recycling the excess reagent to the packed tower and contacting it, preferably in countercurrent, with the vapor from the reaction vessel; optionally recycling the water to the hydrolysis step; also optionally taking the vapors from the overhead collection drum for condensation of water contained therein; and if desired, recycling condensate from the vapors to the hydrolysis step. Recycling these waters from the overhead collection drum to the hydrolysis step may not be preferred if they contain acids, such as formic acid and/or phthalic acid, which may interfere with the ester.

The present invention provides improved techniques for the neutralization and purification of esters which may be produced in such a manner.

The following steps may be employed in addition to the neutralization and preferred first filtration step of this invention: addition of adsorbents such as alumina, silica gel, activated carbon, clay and/or filter aid to the crude ester product mixture; filtration of solids from the ester mixture containing the bulk of the excess reagent (i.e., acid or alcohol) used in the esterification process; removal of the excess reagent from the ester mixture by, for example steam stripping under vacuum and recycling of the excess reagent to the reaction vessel; and removing any residual solids from the stripped ester by means of secondary filtration.

After the ester, which has been neutralized according to the present invention, has been filtered, it may be subject to further purification by stripping, and/or by a further filtration which may employ filter aids and absorbents such as is discussed in our copending PCT patent application WO 2005021482. The purpose of this second filtration is to improve electrical properties while keeping the contents of light ends and odor formers low. Where these techniques are used, materials that may be used as both filter aids and adsorbents include bleaching earths, bentonites or activated clays, containing attapulgite or Fuller's Earth, montmorillonite, kaolinite and muskovite minerals. Examples of adsorbents that may be used are activated alumina, activated china clay, activated carbon, magnesium oxide, aluminium oxide and silicon oxide. These may be used either singly or in combination. The amount of the adsorbent used is preferably between 0.01 and 1% by weight based on the weight of the crude ester. Some of the important clay properties include mineralogy, particle size distribution, surface acidity and degree of heat activation. Heat activation determines the surface area, pore volume, moisture content, and cation exchange capacity. Examples of products that may be used are Engelhard Attasorb® Attapulgite; Pure-Flo® B80 Natural and Pure-Flo® M85/20 both of Oil-Dry Corporation of America; Bensan PER300; and frieTON, FrieBE and frieFood. In particular, we prefer to use the product FrieBE, manufactured from Friedland clay by Friedländer Ton-Industriegesellschaft mbH in Germany. Another preferred product is available from Süd-Chemie AG under the name of TERRANA® 510, which is a natural bleaching earth manufactured by the activation of calcium bentonite.

When this additional purification step is employed we prefer to use from 0.01 to 5 wt % of the adsorbent or the combination of the adsorbent and the filter aid based on the weight of the plasticiser ester to be purified. More preferably we use from 0.02 to 2 wt %, most preferably 0.03 to 1 wt % and in particular. 0.04 to 0.3 wt %. Although the filter aid or the activated carbon may be used alone, we prefer to use a mixture, which mixture preferably contains from 70 to 30 parts by weight of the filter aid and from 30 to 70 parts by weight of the adsorbent. More preferably the mixture contains 60 to 40 parts by weight of the filter aid and from 40 to 60 parts by weight of the absorbent. Our most preferred mixture contains from 40 to 50 parts of the adsorbent, the balance being clay. For cost reasons, a lower content of adsorbent is preferred, but as the level of adsorbent is reduced, also its effect is reduced. We therefore prefer to use at least 30 parts by weight in the mixture. However, when the filter aid is particularly effective by itself, the active carbon may be reduced to as low as 10% by weight of the mixture. We have found that use of the mixture has the additional benefit that it improves the stability of the plasticiser to ultraviolet light, which is particularly important for plasticisers that are used in polyvinyl chloride articles that are intended to be greatly exposed to daylight and particularly to sunlight. A low content of light ends and odor formers is also important when the product is to be used in a confined space such as a space capsule, an aeroplane or truck cabin, a car interior or a greenhouse. When a mixture is used, the filter aid and the adsorbent may be added separately to the plasticiser ester although we prefer that they be added as a mixture as this enables the use of a single injection position in the purification vessel.

The adsorbent and/or the filter aid may be added batchwise, but is preferably added continuously to the ester flowing through a stirred vessel which is optionally provided with baffles to enhance mixing. In one embodiment, this vessel is preferably the neutralization drum.

We have found that by employing the techniques of the present invention, high purity esters may be obtained on an industrial scale in a process in which crude ester is first passed into and through a neutralizing drum where it is contacted with an aqueous solution of sodium carbonate of an amount less than the stoichiometric equivalent of the acidity of the crude ester. We prefer that the solution contains at least 7 and at most 13 wt % of sodium carbonate, more preferably at least 9 and at most 11 wt %, most preferably at least 9.3 wt % and at most 10.7 wt % of sodium carbonate and that it provides from 0.7 to 1.4 wt % water based on the weight of the crude ester. We also prefer that 80%, more preferably 90%, yet more preferably 95%, most preferably 99% of the ester has a residence time in the neutralisation drum of at least 20 minutes. Following the neutralization, water is removed, preferably by flashing off and the material is then filtered preferably through a non metallic filter medium, such as polyvinylidene fluoride. Suitable non metallic filter media are generally of a polymeric nature, for example polyolefins such as polypropylene or polyethylene, polyesters such as PET, PTT, PBT or PEN, fluorocarbon polymers such as Teflon® PTFE, Teflon® FEP, PCTFE, EFTE or PFA, nylons such as PA 4, PA 6, PA 66 or PA 11, polyacetals such as Delrin® POM, polymers like PPO, PPS, PES, PSO, or polycarbonate. Less suitable are PVC or polystyrene, and polyethylene or polypropylene too are less preferred.

We have found that the use of this combination of conditions allows large scale, continuous or semi-continuous purification of esters and enables the production of esters having a sufficiently low alkali metal, e.g. sodium, level to be effective plasticisers for polyisocyanates. Large scale production for isocyanate plasticisers typically employ batch sizes of at least 1 metric tonne of reagents, and those for plasticiser esters typically 15 or more metric tonnes of reagents. Continuous large scale operations employ throughputs of 1 metric tonne per hour or more, typically 4 metric tonnes per hour or more.

In preferred embodiments of the present invention, the process includes a flash step to flash off the free water phase between the neutralization drum and the filter. The removal of the free water is important in the reduction of the build up rate of pressure drop over the filter. The water level is preferably reduced to no more than 500 ppm by weight. The flash step can also remove any remaining or a part of the unreacted alcohol which can be recycled to the esterification reaction. The flash step may be performed in a flash drum and optionally under vacuum. Suitable vacuum pressures for performing this flash step are from 5 to 100 kPa, e.g. from 5 to 60 kPa, such as 5 to 50 or 6 to 30, preferably from 6 to 10 kPa. Optionally the flash step is replaced or complemented by stripping using a stripping vapor such as steam or nitrogen. This stripping may be performed under vacuum conditions similar to those described above, e.g. in a stripping tower into which the ester may optionally be flashed. Alternatively the flash may be performed upstream of the stripping tower, in which case the vapor phases from flash and stripping may be combined and condensed together. Such a stripping tower may be equipped with internals, such as trays and/or structured packing.

An alternative to flashing and /or stripping is the use of a wiped-film evaporator for water removal.

An alternative to removing the water as a vapor is to separate it as a separate liquid phase, in which case the water may contain a significant amount of salt, e.g. of a mono-ester in the case where a di-ester is produced, or depending on pH, of the equivalent acid, e.g. mono-ester. It is preferred to submit this waste water containing mono-ester or its salt to a thermal hydrolysis treatment step, optionally followed by recovery of the alcohol that is liberated from hydrolysing the (salt of the) mono-ester. The hydrolysis of the mono-ester or its salt and recovery of the alcohol also reduce the demand that this waste water may impose on any biological oxidation unit downstream and before disposal.

In a further preferment of the present invention, the neutralization vessel is a vertical drum provided with one or more baffles and/or mechanical stirring to enhance mixing. We prefer that the baffles be horizontal to compartmentalize the vessel, and in a further preference, each compartment is provided with a stirrer or mechanical mixing device. The crude ester is preferably injected into the top of the vessel and the alkali metal salt, preferably soda ash, and water, is preferably injected into the stream of crude ester shortly before it enters the vessel. The vessel is preferably at a temperature in the range 100° C. to 140° C., more preferably 110 to 130° C., and most preferably 120 to 125°, and the pressure in the vessel should be sufficient to prevent the water vaporizing. Typical pressure is between 4 and 10 barg, preferably from 5 to 6 or 7 barg, more preferably from 5.5 to 5.8 barg. The amount of alkali metal salt, e.g. sodium carbonate, that is used should be less than the stoichiometric amount in relation to the acidity of the crude ester. The preferred amount depends upon the type of ester, the speed of flow of the crude ester, the temperature in the neutralization drum and the residence time of the ester in the drum. However, it is important not to use more alkali metal salt (soda ash) than is required for the neutralization since this can lead to residual alkali metal (sodium) or base in the ester and to the formation of haze in the purified ester.

The amount of water that should be present during treatment, which is in practical terms the amount added, is from 0.7 to 1.4 wt % based on the weight of crude ester. The preferred amount of water depends on the nature of the ester and the concentration and type of catalyst used. Relative to the total feed rate of crude ester to the hydrolysis drum and expressed in weight percent, the preferred and more preferred amounts of hydrolysis water are as stated in Table 1. They depend also on the catalyst concentration used. For each grade, the numbers are given for two levels of tetra-isooctyl-titanate used, which is expressed in % wt titanium relative to the amount of phthalic anhydride reagent used in the esterification reaction. The percentage of hydrolysis water may also be adjusted slightly downward if throughput is reduced. Because the catalyst represents an important cost element in the production of a phthalate ester, when throughput is reduced there is interest in reducing the catalyst concentration and extending the reaction time. With a lower catalyst concentration, also less water is needed for hydrolysis of the catalyst. These adjustments all contribute to a smooth and slow buildup of pressure drop over the filter.

TABLE 1

| Ester produced | Catalyst Concentration | Preferred wt % Water | More preferred wt % Water |
|---|---|---|---|
| C7 phthalate | 0.016-0.017% wt | 1.0-1.4 | 1.2-1.4 |
|  | 0.030-0.033% wt | 1.1-1.4 | 1.3-1.4 |
| C9 phthalate | 0.018-0.019% wt | 0.9-1.3 | 1.1-1.2 |
|  | 0.034-0.037% wt | 1.1-1.4 | 1.2-1.3 |
| C10 phthalate | 0.018-0.019% wt | 0.9-1.3 | 1.0-1.1 |
|  | 0.035-0.037% wt | 1.0-1.4 | 1.1-1.2 |
| C11 phthalate | 0.019-0.021% wt | 0.8-1.3 | 0.95-1.05 |
|  | 0.037-0.039% wt | 0.9-1.4 | 1.05-1.15 |

All catalyst concentrations in Table 1 are expressed as wt % titanium on phthalic anhydride charged into the reactor. The water is expressed as wt % on crude ester. It is preferably controlled very tightly down to an accuracy of 0.01% or below, using appropriately accurate instrumentation such as e.g. a coriolis flow meter. Variations within the ranges given in Table 1 are still applied, based on results of acidity measurement on the crude ester, measurement of the soda ash concentration, on actual catalyst dosing of the particular batch, on filter history and runlength, on throughput requirements and on experience.

We have also found that, in order to avoid undue filtration resistance, it is desirable that the filter medium be non-metallic For example, it may be polymeric and woven or nonwoven. In a preferred operation the filtration medium is polyvinylidene fluoride such as in DrM® filters employing a core of stainless steel tubes or candles covered with a sock or hose of polyvinylidene fluoride. Many filters similar to DrM filters are known and available commercially. We have found that when such a filter is used together with the conditions of the present invention, excellent filtration at an acceptable speed can be achieved, with the production of an easily handleable filter cake. We also prefer to compact the filter cake, before discharge from the filter, with an inert gas such as nitrogen, to press and dry the cake. This has been found to further improve the handlability of the cake and to ease disposal such as by incineration or reuse as a filler, for example in a polyvinyl chloride compound or article. This compacting and drying of the filter cake reduces ester losses, and also reduces the risk that the filter cake after dumping and exposing to air would excessively heat up and start fuming/smoking. The compacting is preferably not done with a gas that contains oxygen, such as air, because to do so would create a possible risk of developing a fire, by auto-ignition, in the filters and/or in the cake box after dumping the cake. An additional benefit of the use of the techniques of the present invention is that they allow accurate prediction of when the filter needs to be decommissioned or switched according to the nature of the ester, so that filter switching can be automated. Ideally, the filter is decommissioned after a certain cumulative throughput, representative of an equivalent amount of solids that have been collected on the filter device. Pressure drop over the filter device is continuously monitored, and the filter is preferably switched out of service if the pressure drop exceeds a given value, determined by experience. As a third criterion, a certain time-on-stream for each filter service is ideally not exceeded. These criteria are applied in order to avoid excessive solids buildup on the filter device, and/or a too dense filter cake which is too sticky and too strongly attached to the filter cloth or device. In both cases, filter cleaning becomes problematic.

A normal filter decommissioning procedure comprises the following sequence: the pumping of the product stream through the filter is stopped, and liquid is drained from the vessel, being replaced by nitrogen. Nitrogen is then pushed through the filter from the dirty side to the clean side. This compresses the filter cake, pushing more liquid out and drying the cake. Any residual liquid is then drained from the vessel. The filter vessel is then opened. Nitrogen pressure is then provided from the clean side of the filter device. This blows up the filter cloth and expands the filter cake, so that the filter cake falls apart in smaller pieces and collects, ideally as a dust, in a collection bin provided underneath the opened filter device.

If too much solid material has collected on the filter device, there may not be sufficient vapor space left between individual filter elements, such as plates or candles, for the filter cake to expand and fall apart. In that case, the filter device may need to be rinsed with a suitable liquid, such as hot condensate, resulting in a slurry to be disposed of as chemical waste; or the filter device needs to be opened and dismantled and the filter cake removed mechanically, if necessary by hammering. Dismantling may involve removal of headers and other internals, and lifting out of filter sections or candles, if necessary one by one. The high extra burden relative to a normal filter operation provides a significant incentive for the operations according to the present invention.

Titanium residues in plasticisers have been found to result in colour formation in the plasticisers during storage particularly if heating is required during storage, as may be required in cold climates, or in the case of higher molecular weight plasticisers such as $C_{11}$ and particularly $C_{13}$ phthalates.

Antioxidants such as phenolic antioxidants are typically incorporated into plasticiser esters which are to be stored and used in particular end uses such as wire and cable production. We have found that colour formation may occur, despite the presence of antioxidant, if the plasticiser contains titanium residues. This is thought to be due to interaction of the titanium with the antioxidant. Although the thermal stability of the plasticiser is not significantly affected, the discoloration of heated plasticiser may create problems for the PVC compounding and cable industry, in particular when making white or transparent compounds. The techniques of the present invention have been found to provide methods by which the titanium levels in the plasticiser may be reduced to below the level which results in the above-described colour formation. We have found that by providing a titanium level below 0.01 ppm by weight of titanium in the ester product, colour formation in the presence of an antioxidant may be substantially reduced or even avoided.

Accordingly, in a further embodiment, the present invention provides a storage stable plasticiser composition comprising a C6 to C13 phthalate ester prepared by titanium catalysed esterification containing less than 0.01 ppm by weight of titanium and containing from 0.1 to 2.0 wt % of an antioxidant. The titanium content is typically determined by ICP-AES (Inductively Coupled Plasma Atomic Emission Spectrometry). The antioxidant content is conveniently determined by HPLC (High Performance Liquid Chromatography). We prefer to use a Waters 2695 separation module, equipped with a Nova-Pak C18 60 Angstrom 4 micrometer (3.9×150 mm) column and a Photodiode Array Detector. We prefer to use 278 nm as testing wavelength, where most typical antioxidants give a convenient reading. The mobile phase and operating procedure may be adapted to the nature of the antioxidant that is being analysed for. As procedure, either an isocratic run or a gradient run may be used. For many of the typical antioxidants we prefer to use a gradient run with a flow rate of 1 ml/min, and as mobile phase an 80/20 or 90/10 vol % methanol/water mixture for the first 2.5 minutes at the start of the run and for the last 3 minutes at the end of the run, separated by a 100% methanol mobile phase for the 12.5 minutes middle section of the run. When isocratic runs are carried out, we prefer to operate with 100% methanol as mobile phase at a flow rate of 2 ml/min for the full run. Quantification may conveniently be done with reference to an external standard that is prepared and analyzed separately.

A plasticiser prepared by titanium catalysed esterification typically contains a small amount of co-ester of the diacid on one side esterified with a molecule from the parent alcohol of the plasticiser di-ester, and on the other side esterified with a molecule from the titanium alcoholate catalyst that was used. In many cases the alcohol from the catalyst is different by 2 or more carbon numbers, usually containing fewer carbon atoms but alternatively more, and hence has a distinctly lower (or higher) molecular weight than the parent alcohol of the plasticiser. The co-ester is therefore typically also of a distinctly lower (or higher) molecular weight than the major plasticiser ester. This co-ester will clearly show up as a separate peak or set of peaks in a standard plasticiser boiling point GC spectrum usually before or on the shoulder of the main plasticiser peak or set of peaks, on the light end side of it, or alternatively on the heavy end side of it or on the heavy end side shoulder of the main ester peak or peaks. Typical co-esters are co-esters with isopropanol, normal- or iso-butanol, normal- and/or iso-octanol, or 2-ethyl-hexanol. Typical concentrations of these co-esters are 50 to 2500 ppm by weight, preferably 100 to 2000 ppm by weight, more preferably 200 to 1500 ppm by weight, and most preferably 300 to 1200 ppm by weight. Co-ester levels above 1000 ppm are less preferred because they may then, e.g. as a C10/C4 co-ester in a C10 phthalate, contribute to the light scattering film (LSF) or fogging performance of the plasticiser and of articles made therewith.

We prefer to use from 0.1 to 1.5 wt %, more preferably 0.2 to 0.75 wt % of the antioxidant and we further prefer that the antioxidant is a phenolic antioxidant. Examples of preferred antioxidants are compounds such as di-tert-butyl hydroxy toluene or "butylated hydroxytoluene" (BHT), "butylated hydroxy ethylbenzene (BHEB), or the following compounds: Bis-phenol-A (BPA), diphenylolpropane or 2,2-Bis (p-hydroxyphenyl) propane); Topanol CA (TCA, or 1,1,3-tris (2-methyl-4-hydroxy-5-t-butylphenyl) butane); Irganox® 1010 (tetrakis-(methylene (3,5-di-t-butyl-4-hydroxyhydrocinnamate) methane); Irganox® 1076 (octadecyl-3,5-di-t-butyl-4-hydroxyhydrocinnamate); Irganox 1135 (benzenepropanoic acid, 3,5-bis(1,1-dimethyl-ethyl)-4-hydroxy-C7-C9 branched alkyl esters); Irganox® 1141 (2,4-dimethyl-6-(1-methylpentadecyl)-phenol); tris-(3,5-di-tert-butyl-4-hydroxybenzyl)isocyanurate; tris-(4-tert-butyl-3-hydroxy-2,6-dimethylbenzyl)isocynanurate and 1,3,5-[tris(para-4-hydroxy-3,5-tert-butyl benzyl] 2,4,6-trimethyl benzene.

EXAMPLES

The present invention is illustrated by reference to the following examples.

Example 1

This describes an operation without using the improvements according to the present invention. All data below apply to all grades mentioned in Table 1:

| | |
|---|---|
| Hydrolysis water ratio | 3-5 wt % on crude ester |
| Sodium carbonate | 2 to 3 times the stoichiometric amount of acidity in the crude ester |
| Hydrolysis temperature | 120-140 C. |
| Hydrolysis pressure | 6 barg |

For the filtration operation the following parameters apply:

| | |
|---|---|
| Active carbon addition | 0.02 wt % on crude ester |
| Filter aid (Perlite) | 0.03-0.08 wt % on crude ester |
| Maximum allowable pressure drop over the filter: | 3 bar |

The finished plasticiser product produced according to this example contained from 3-5 ppm sodium with a product acidity of 0.01-0.02 mg KOH/g. This product caused premature polymerization when the product was mixed with isocyanate monomer. The high sodium content also became visible as a haze upon cooling down to ambient temperature and given sufficient time, after several days. Run lengths of the first filters following the hydrolysis/neutralisation step were in the order of 2-2.5 metric tonnes of crude ester processed per square meter of filter area in the filter device.

Example 2

This describes the operation after the improvements according to the present invention have been made. All data below apply to all grades as mentioned in Table 1:

| | |
|---|---|
| Hydrolysis water ratio | Within the ranges given in Table 1, column headed "Preferred wt % water", as wt % on crude ester |
| Sodium carbonate | Less than the stoichiometric amount of acidity in the crude ester |
| Hydrolysis temperature | 120-130 C. |
| Hydrolysis pressure | 4-6.5 barg |

For the filtration operation the following parameters apply:

| | |
|---|---|
| Active carbon addition | 0.02 wt % on crude ester |
| Filter aid (Perlite) | 0.01 wt % on crude ester |
| Maximum allowable pressure drop over the filter: | 5 bar |
| Maximum allowable cumulative throughput: | 10.3 ton/m2. |

The finished plasticiser product from this example contained less than 0.2 ppm sodium with a product acidity of 0.03-0.05 mg KOH/g. It did not cause any premature polymerization when the product was mixed with isocyanate monomer. The run lengths of the first filters following the hydrolysis/neutralisation step increased from 2-2.5 to the order of 10 metric tonnes of crude ester processed per square meter of filter area present in the filter device.

The invention claimed is:

1. A storage stable plasticiser composition comprising a $C_{13}$ phthalate ester containing titanium but in an amount less than 0.01 ppm by wt of titanium, prepared by titanium catalysed esterification, and containing from 0.1 to 2.0 wt % of an antioxidant; wherein said titanium range reduces or avoids colour formation in the storage stable plasticiser.

2. The composition according to claim 1 comprising from 50 to 2500 ppm by weight of a second phthalate ester formed from an alcohol having at least 2 carbon atoms more or at least 2 carbon atoms fewer than the alcohol used to form the $C_{13}$(first) phthalate ester of the plasticiser.

3. The composition according to claim 1 containing from 0.2 to 0.75 wt % of the antioxidant.

4. The composition according to claim 1 in which the antioxidant is a phenolic antioxidant.

5. The composition according to claim 1 which has been prepared by a method wherein esterification is followed by a purification process.

6. The composition according to claim 1 comprising from 50 to 2500 ppm by weight of a second phthalate ester formed from an alcohol having at least 2 carbon atoms more or at least 2 carbon atoms fewer than the alcohol used to form the $C_{13}$(first) phthalate ester of the plasticiser and containing from 0.2 to 0.75 wt % of the antioxidant.

* * * * *

UNITED STATES PATENT AND TRADEMARK OFFICE
CERTIFICATE OF CORRECTION

PATENT NO. : 7,919,649 B2  Page 1 of 1
APPLICATION NO. : 11/398235
DATED : April 5, 2011
INVENTOR(S) : Brady Compton et al.

It is certified that error appears in the above-identified patent and that said Letters Patent is hereby corrected as shown below:

Assignee should read: ExxonMobil Chemical Patents Inc.
Houston, TX (US)

Signed and Sealed this
Fifth Day of July, 2011

David J. Kappos
*Director of the United States Patent and Trademark Office*

UNITED STATES PATENT AND TRADEMARK OFFICE
CERTIFICATE OF CORRECTION

PATENT NO. : 7,919,649 B2  
APPLICATION NO. : 11/398235  
DATED : April 5, 2011  
INVENTOR(S) : Brady Compton et al.

It is certified that error appears in the above-identified patent and that said Letters Patent is hereby corrected as shown below:

Title Page, Item (73) Assignee should read:   --ExxonMobil Chemical Patents Inc.
                                                Houston, TX (US)--

This certificate supersedes the Certificate of Correction issued July 5, 2011.

Signed and Sealed this
Sixteenth Day of August, 2011

David J. Kappos
*Director of the United States Patent and Trademark Office*